(12) United States Patent
Murayama et al.

(10) Patent No.: US 10,184,885 B2
(45) Date of Patent: Jan. 22, 2019

(54) INFORMATION PROCESSING DEVICE TO PROCESS SPECTRAL INFORMATION, AND INFORMATION PROCESSING METHOD

(71) Applicant: CANON KABUSHIKI KAISHA, Tokyo (JP)

(72) Inventors: Yohei Murayama, Kawasaki (JP); Kota Iwasaki, Atsugi (JP); Masafumi Kyogaku, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 326 days.

(21) Appl. No.: 14/901,015

(22) PCT Filed: Jun. 23, 2014

(86) PCT No.: PCT/JP2014/003370
§ 371 (c)(1),
(2) Date: Dec. 22, 2015

(87) PCT Pub. No.: WO2014/208077
PCT Pub. Date: Dec. 31, 2014

(65) Prior Publication Data
US 2017/0322146 A1 Nov. 9, 2017

(30) Foreign Application Priority Data

Jun. 26, 2013 (JP) .................................. 2013-133542
May 14, 2014 (JP) .................................. 2014-100829

(51) Int. Cl.
*G01N 21/65* (2006.01)
*G01N 21/31* (2006.01)
(Continued)

(52) U.S. Cl.
CPC ............. *G01N 21/31* (2013.01); *G01N 21/27* (2013.01); *G01N 21/65* (2013.01); *G01J 3/02* (2013.01);
(Continued)

(58) Field of Classification Search
CPC ........ G01N 21/64; G01N 21/65; G01N 21/31; G01N 21/27; G01J 3/02; G01J 3/44
See application file for complete search history.

(56) References Cited

U.S. PATENT DOCUMENTS

2011/0216952 A1* 9/2011 Kajihara .................. G06K 9/00
382/128

FOREIGN PATENT DOCUMENTS

JP 2008-523474 A 7/2008
JP 2011-2341 A 1/2011
(Continued)

*Primary Examiner* — Abdullahi Nur
(74) *Attorney, Agent, or Firm* — Canon U.S.A., Inc. IP Division

(57) ABSTRACT

An information processing device configured to process spectral information includes: a data obtaining unit configured to obtain three-dimensional distribution data of spectral information; a generating unit configured to generate two-dimensional image, data from the three-dimensional distribution data of spectral information; a display unit; a display control unit configured to display the two-dimensional image on the display unit; an information obtaining unit configured to obtain position information of a two-dimensional region which a user has selected from the two-dimensional image; and an extracting unit configured to extract, from a three-dimensional region corresponding to the two-dimensional region, in the three-dimensional distribution of spectral information, feature region information satisfying predetermined feature conditions.

21 Claims, 10 Drawing Sheets

(51) Int. Cl.
*G01N 21/27* (2006.01)
*G01J 3/02* (2006.01)
*G01J 3/44* (2006.01)
*G01N 21/64* (2006.01)

(52) U.S. Cl.
CPC ........ *G01J 3/44* (2013.01); *G01N 2021/6423* (2013.01)

(56) References Cited

FOREIGN PATENT DOCUMENTS

| | | |
|---|---|---|
| JP | 2013-68529 A | 4/2013 |
| WO | 2009/004874 A1 | 1/2009 |

\* cited by examiner

INFORMATION PROCESSING DEVICE TO PROCESS SPECTRAL INFORMATION, AND INFORMATION PROCESSING METHOD

CROSS REFERENCE TO RELATED APPLICATIONS

This application is a National Stage filing of International Application No. PCT/JP2014/003370 filed Jun. 23, 2014, which claims the benefit of priority from Japanese Patent Application No. 2013-133542 filed Jun. 26, 2013, and Japanese Patent Application No. 2014-100829 filed May 14, 2014, the disclosures of each of which are hereby incorporated by reference herein in their entirety.

TECHNICAL FIELD

The present invention relates to an information processing device to process spectral information, and an information processing method.

BACKGROUND ART

There have been developed spectroscopy microscopes which visualize two-dimensional distribution of structures included in tissue, such as cell nuclei, cytoplasm, fiber, and so forth, by spectroscopy such as Raman scattering spectroscopy. Spectroscopy microscopes yield spectral information owing to molecules included in the structures, in addition to morphology information of the structures. This information enables tissue to be distinguished free of dyes. However, two-dimensional distribution only includes information of a particular cross-section, so the morphology information of the structure may be insufficient for distinguishing the structure at a higher level of accuracy. As an attempt to solve this, three-dimensional spectroscopic measurement aims to obtain three-dimensional distribution of spectral information. Such three-dimensional spectroscopic measurement may be performed by first obtaining two-dimensional distributions for a great number of adjacent tissue sections, and then re-constructing these, or by obtaining multiple Z-stack images (different images at multiple Z-positions) of a specimen, for example. Three-dimensional distribution images have three-dimensional form information unattainable by two-dimensional distribution, so structures can be distinguished at a high level of accuracy.

When analyzing three-dimensional distribution images of spectral information, a spectroscopic microscope user specifies a feature region in a three-dimensional distribution image, and distinguishes structures based on three-dimensional form and spectral information (wavelength, signal intensity, spectrum, etc.) of that feature region.

Technology to assist specifying of feature regions in three-dimensional distribution images of spectral information has been disclosed PTL 1 discloses a system which specifies and displays a three-dimensional region of a light emission source as a feature region. According to PTL 1, three-dimensional position information of a light emission source existing within the specimen is automatically calculated using spectroscopic spectrums, which facilitates specifying a light emission source. PTL 2 discloses a system where a spectroscopic spectrum of a reference sample is referenced, and a region of the specimen having a spectroscopic spectrum similar e reference sample is displayed as a feature region.

CITATION LIST

Patent Literature

PTL 1: PCT Japanese Translation Patent Publication No. 2008-523474
PTL 2: Japanese Patent Laid-Open No. 2011-2341

SUMMARY OF INVENTION

Technical Problem

The operation of specifying feature regions is troublesome in performing analysis of three-dimensional distribution images obtained by spectroscopy microscopes, often making analysis difficult. The reason is that three-dimensional display images are displayed as two-dimensional images on the display screen. The user cannot readily visually recognize the depth information which the three-dimensional distribution has, and accordingly it becomes difficult for the user to specify an intended feature region and obtain spectral information.

The system described in PTL 1 is only effective in a case where the structure includes luminescent molecules, and accordingly is inapplicable to distinguishing most structures. Also, the spectroscopic spectrum displayed in the system described in PTL 1 is a spectrum obtained by integrating all data of a three-dimensional distribution image projected onto a two-dimensional plane. That is to say, the spectroscopic spectrum is not a spectrum of a feature region at a particular three-dimensional position, but rather is a spectrum including information of regions other than the feature region as well. Accordingly, PTL 1 is not readily applied to analysis to distinguish structures.

The system described in PTL 2 cannot be used for detailed analysis such as the user optionally specifying a region, and spectral information in a feature region existing in that region being configured.

Solution to Problem

It has been found desirable to provide an information processing device which processes three-dimensional distribution data so that feature regions in three-dimensional distribution images of spectral information can be easily specified.

An information processing device according to the present invention is configured to process spectral information. The information processing device includes: a data obtaining unit configured to obtain three-dimensional distribution data of spectral information; a generating unit configured to generate two-dimensional image data from the three-dimensional distribution data of spectral information; a display unit; a display control unit configured to display the two-dimensional image on the display unit; an information obtaining unit configured to obtain position information of a two-dimensional region which a user has selected from the two-dimensional image; and an extracting unit configured to extract, from a three-dimensional region corresponding to the two-dimensional region, in the three-dimensional distribution of spectral information, feature region information satisfying predetermined feature conditions.

Further features of the present invention will become apparent from the following description of exemplary embodiments with reference to the attached drawings.

DESCRIPTION OF EMBODIMENT

An embodiment of the present invention will be described in detail with reference to the drawings. While an embodiment will be described primarily regarding processing of data including wavelength information obtained by spectroscopy, the method of obtaining data is not restricted in the present invention, and mass spectrometry may be employed instead. That is to say, the spectral information according to the present invention may include mass information, and signal intensity at each mass. The device according to the present invention handles mass information in the same way as it does wavelength information, and thus can process mass spectrometry data in the same way as the data processing described in the embodiment.

Figure 1:
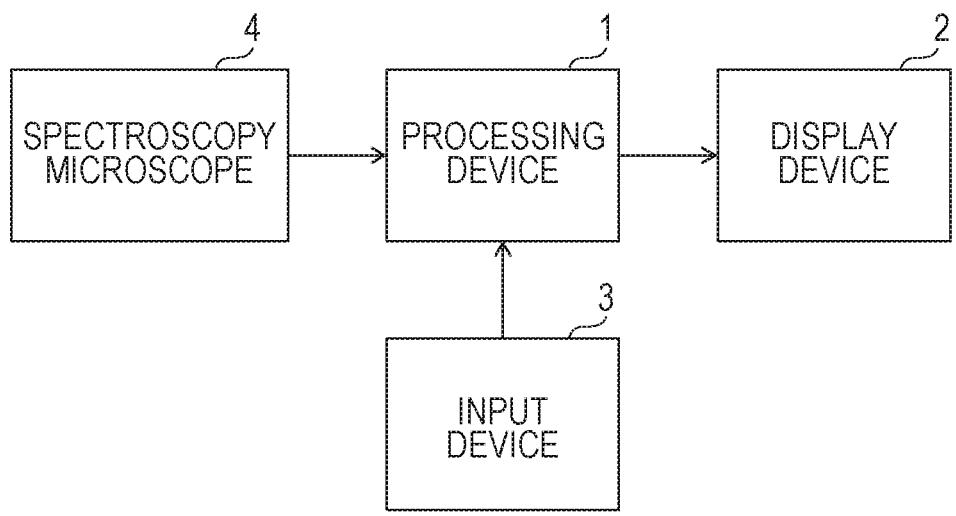
FIG. 1 is a diagram illustrating a microscope system according to the present invention.

FIG. 1 illustrates a microscope system 100 according to the present embodiment. The microscope system 100 includes a spectroscopy microscope 4, a processing device 1, a display device 2, and an input device 3.

The spectroscopy microscope 4 is a measurement device to obtain spectral information of a specimen. The spectroscopy microscope 4 obtains three-dimensional distribution data of spectral information. An example of the spectroscopy microscope 4 is a Raman spectroscopy microscope. The spectroscopy microscope 4 will be described in detail later.

The processing device 1 is an information processing device which processes the spectral information obtained by the spectroscopy microscope 4. The processing device 1 is not restricted in particular as long as it is a device which process spectral information, and may be a dedicated device, or may be a general-purpose personal computer (PC). In a case where the spectroscopy microscope 4 is a PC, the spectroscopy microscope 4 may also serve as a control unit of the spectroscopy microscope 4, or may be dedicated to analysis. The processing device 1 will be described in detail later.

The display device 2 is a device which displays images to prompt a user to perform input, and also displays two-dimensional images generated at the processing device 1. The display device 2 is not restricted in particular as long as it is a display having a two-dimensional face, and may be a general PC display. The display device 2 also may be configured including multiple display devices, such as a PC multi-monitor arrangement. The user can optionally set images for user input, two-dimensional images, objects for displaying information and so forth, to be displayed on each display device.

The input device 3 is configured including devices capable of various types of instructions, such as a keyboard, mouse, dedicated controller (e.g., trackball, touchpad) or the like. The user inputs information to control the operations of the processing device 1 from the input device 3. The input device 3 is a device for the user to select data and to input signals to the processing device 1 to perform analysis based on the images and information displayed on the display device 2.

Figure 9:
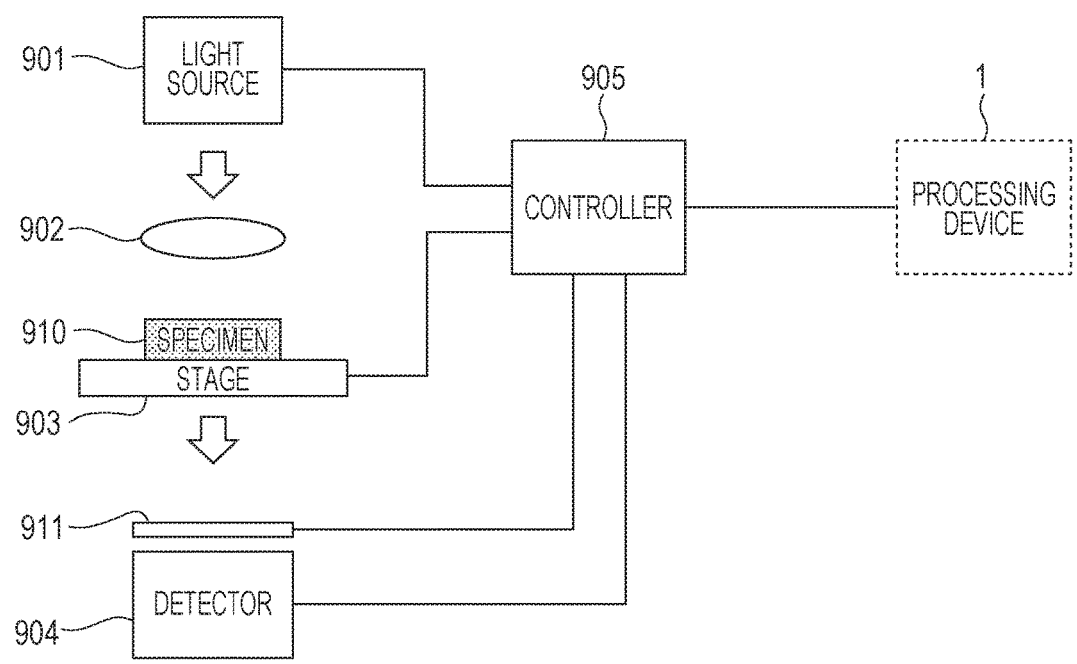
FIG. 9 is a diagram illustrating a spectroscopy microscope according to the present invention.

First, the spectroscopy microscope 4 will be described in detail with reference to FIG. 9. FIG. 9 is a diagram which illustrates the spectroscopy microscope 4 according to the present embodiment in FIG. 4.

The spectroscopy microscope 4 is a device which obtains spectral information (spectroscopic spectrum) of a specimen 910. The spectroscopy microscope 4 includes a light source 901, an optical system 902, a stage 903, a detector 904, a controller 905, and a spectral element 911.

The light source 901 generates electromagnetic rays to irradiate on the specimen 910. The light source 901 may be a variable-wavelength light source, or may be a white-light light source emitting electromagnetic rays of broadband wavelengths. Examples include a halogen lamp, a deuterium lamp, an infrared lamp, a laser, a light-emitting diode, or the like. These may be combined and used. Light from the light source 901 is shaped as appropriate at the optical system 902, and cast upon the specimen 910 held on the stage 903.

The stage 903 moves while holding the specimen 910. As the stage 903 moves, the measurement region on the specimen 910 moves. Note that the measurement region may be changed by adjusting the optical system 902. The stage 903 is configured so as to be movable in not only directions perpendicular to the optical axis (X-Y directions) but also in the direction parallel to the optical axis (Z direction). Moving the stage 903 in the Z direction allows multiple so-called Z-stack images to be obtained, and a three-dimensional distribution of spectral information to be obtained.

The detector 904 is a detector which outputs signals when detecting electromagnetic rays. An example of a semiconductor detector which can be used is a photodiode, or the like. In a case of using a photodiode, light from each measurement region is measured, whereby an image can be obtained corresponding to the entire measurement region where each measurement region is one pixel. Alternatively, in a case of using an area sensor such as a charge-coupled device (CCD) or complementary metal-oxide semiconductor (CMOS) device, or a line sensor or the like, as the detector 904, an image can be obtained corresponding to the entire measurement region where each pixel of the sensor is one pixel, even without changing the measurement region.

The spectral element 911 is situated between the detector 904 and the specimen 910. In a case where the light source 901 is a white-light light source, the detector 904 performs detection multiple times while the transparent wavelength of the spectra element 911 is changed, thereby measuring the spectral information at each pixel. If the light source 901 is a variable-wavelength light source, the spectral element 911 does not need to be used. In this case, the detector 904 performs detection multiple tunes while the wavelength of the light source 901 is changed, thereby measuring the spectral information at each pixel.

The controller 905 controls the light source 901, stage 903, spectral element 911, and detector 904. The controller 905 obtains position information of the stage 903, correlates the position information with spectral information, and generates three-dimensional distribution data of the spectral information. In a case where the detector 904 is an area sensor, the controller 905 obtains position information of each pixel of the sensor, correlates the position information with spectral information, and generates three-dimensional distribution data of the spectral information. The controller 905 then transmits the three-dimensional distribution data of the spectral information to the processing device 1.

Figure 2:
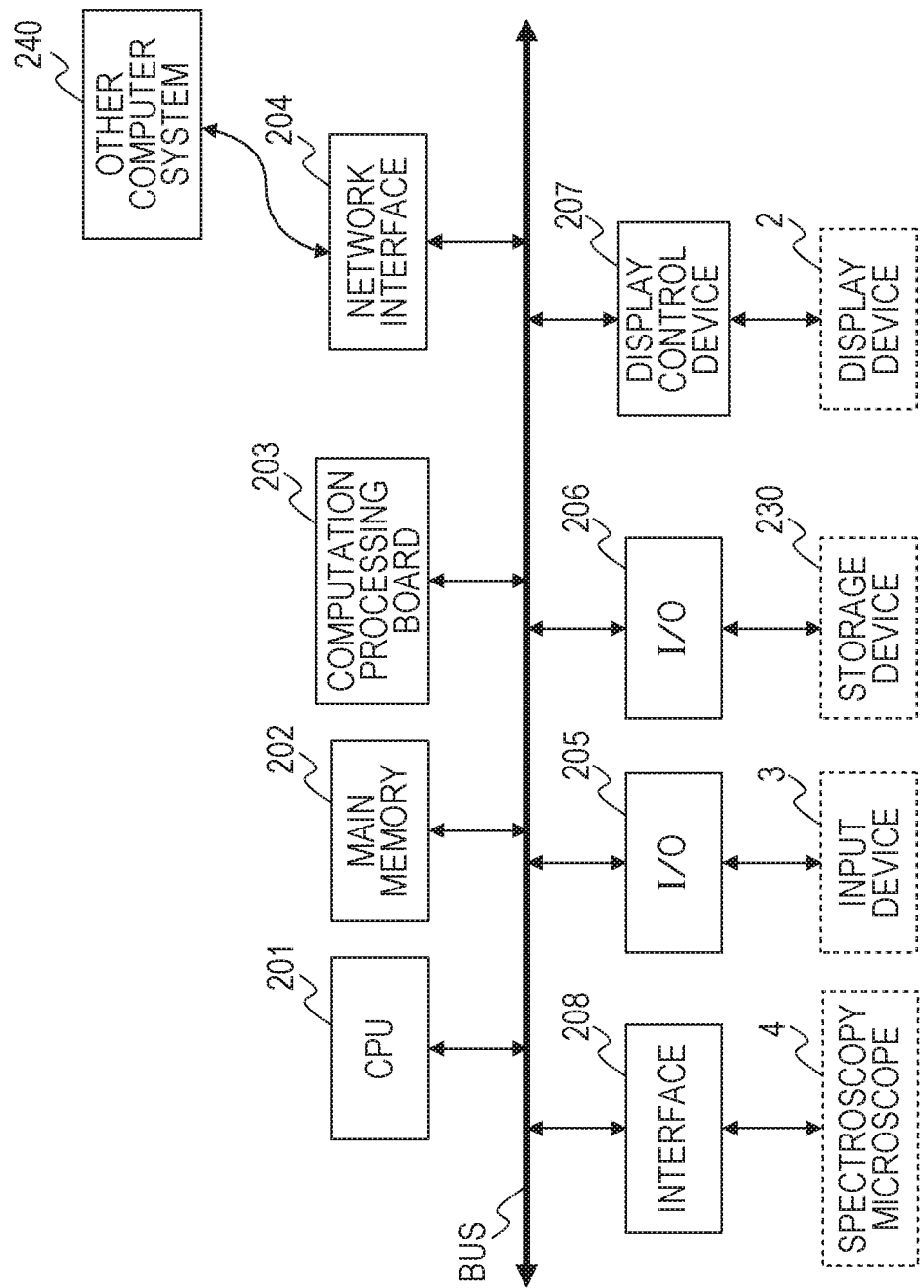
FIG. 2 is a diagram illustrating the internal configuration of the processing device according to the present invention.

Next, the processing device 1 will be described in detail with reference to FIGS. 2 and 3. FIG. 2 is a diagram illustrating the inner configuration of the processing device 1.

A central processing unit (CPU) 201 controls the overall processing device 1 using programs and data stored in main memory 202. The CPU 201 also performs later-described computation processing, data processing, and so forth.

The main memory 202 includes a storage area to temporarily stored programs and data loaded from a storage device 230, and programs and data downloaded from another computer system 240 via a network interface 204. The main memory 202 also includes a work area which the CPU 201 needs to perform various types of processing. The storage device 230, which is a hard disk, optical drive, flash memory, or the like, is connected to the processing device 1, as well as the other computer system 240 which can be accessed via the network interface 204. FIG. 2 illustrates the storage device 230 as being an external device from the processing device 1, but may be built into the processing device 1.

An I/O 205 is a port used to notify various types of instructions and so forth, input through the input device 3, to the CPU 201.

The storage device 230 is a large-capacity information storage device such as a hard disk or the like, and stores an operating system (OS), information processing programs to cause the CPU 201 to perform later-described processing, spectral information, and so forth. Writing information to the storage device 230, and reading information from the storage device 230, is performed through an I/O 206.

A display control device 207 performs control to display images and text and the like on the display device 2.

An external interface may be connected to an interface 208 to acquire output signals of the spectroscopy microscope 4 (spectral information of the specimen which the spectroscopy microscope 4 has obtained). Examples of interfaces which can be used include serial interfaces such as Universal Serial Bus (USB) and IEEE1394, a camera link, or the like. Alternatively, the interface 208 may be an A/D conversion interface, to which output signals of the spectroscopy microscope 4 are input via a coaxial cable or the like. The spectroscopy microscope 4 is connected to the processing device 1 through such an interface 208.

A computation processing board 203 has a processor which has been reinforced regarding specific computation functions, such as image processing or the like, and buffer memory. Description will be made below regarding an arrangement where computation processing, data processing, and so forth, are performed by the CPU 201 using the main memory 202 as memory area, but an arrangement may also be made where the processor and buffer memory on the computation processing board 203 is used, and this arrangement is within the scope of the present invention as well.

An information processing program, which is a computer program, is executed at the processing device 1. This information processing program is stored in an internal storage device within the processing device 1, or an external storage device. The functions relating to the later-described information processing are provided by this information processing program, and the functions of the information processing program can be called up (used) by way of an image display application. The processing results of the information processing program (e.g., images of extracted feature regions) are presented to the user by way of the image display application.

Figure 3:
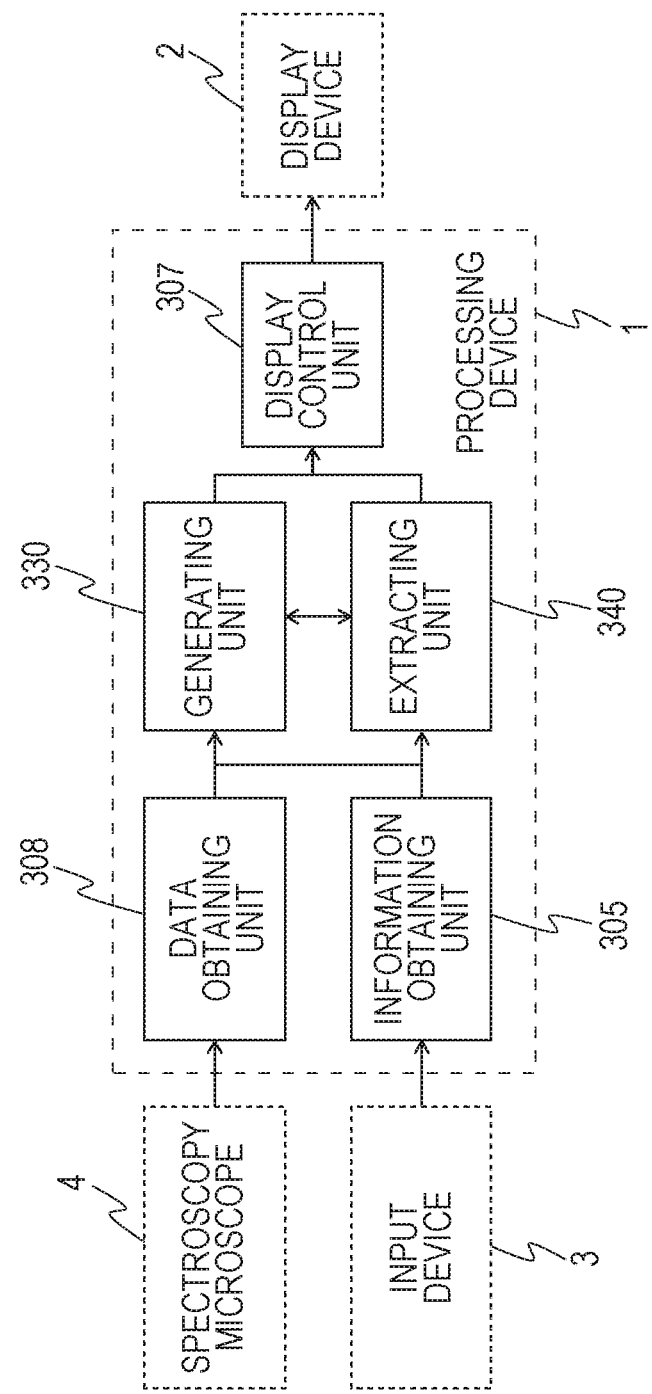
FIG. 3 is a function block diagram illustrating a processing device according to the present invention.

FIG. 3 is a function block diagram of the processing device 1.

A data obtaining unit 308 obtains the three-dimensional distribution data of the spectral information which the spectroscopy microscope 4 has obtained. An information obtaining unit 305 obtains information (signals) which the user has input at the input device 3. A generating unit 330 generates two-dimensional image (display image) data, based on the three-dimensional distribution data of spectral information which the data obtaining unit 308 has obtained, and user instructions which the information obtaining unit 305 has obtained. An extracting unit 340 extracts feature regions from the three-dimensional distribution of the spectral information, based on the three-dimensional distribution data of spectral information which the data obtaining unit 308 has obtained, and user instructions which the information obtaining unit 305 has obtained. A display control unit 307 performs control to display the display images generated at the generating unit 330, and images of feature regions extracted at the extracting unit 340, on the display device 2.

Figure 4:
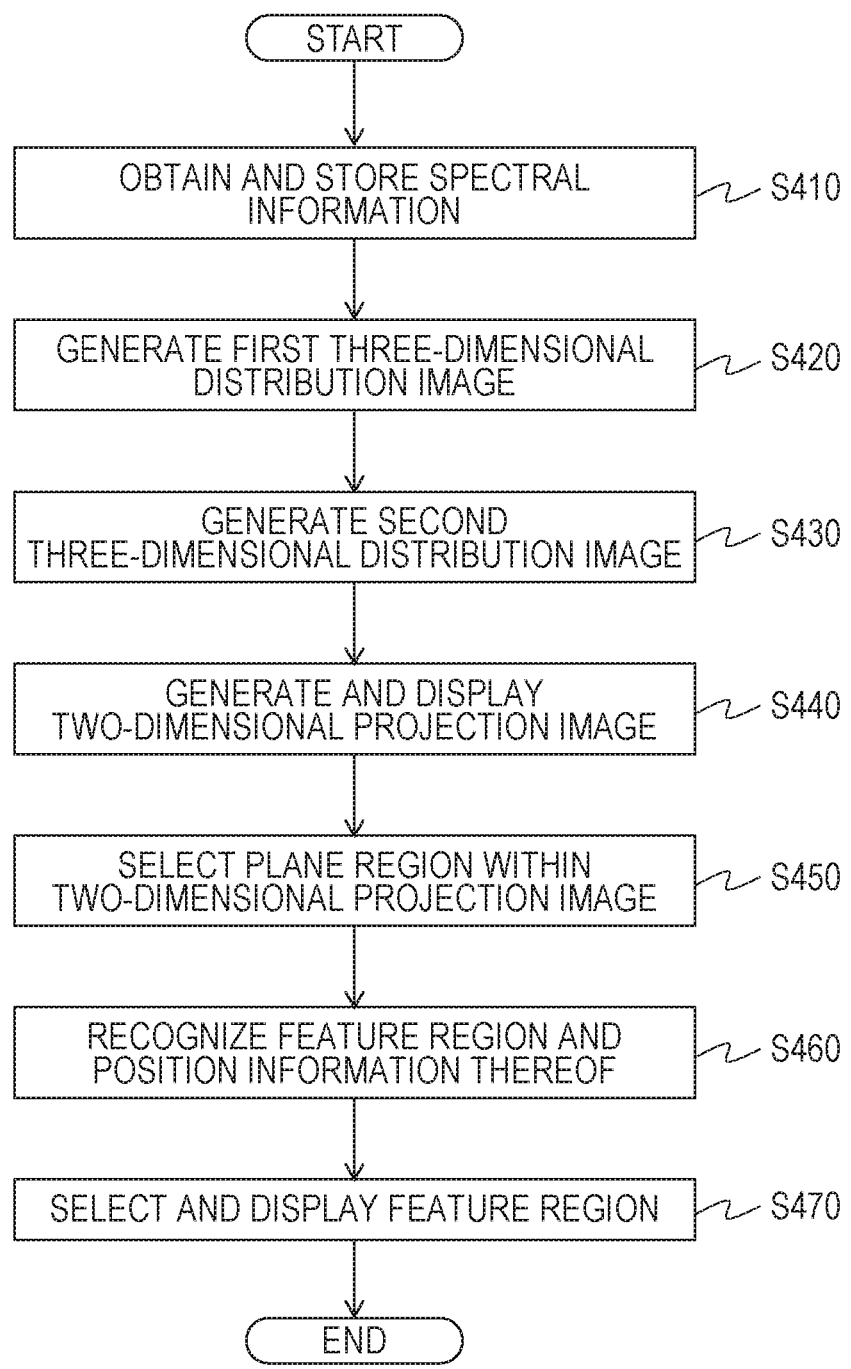
FIG. 4 is a flowchart of operations in an information processing method according to the present invention.

FIG. 4 is a flowchart illustrating the information processing method according to the present embodiment. Each step in FIG. 4 will be described here.

Obtaining and Storing Spectral Information: S410

The CPU 201 (data obtaining unit) of the processing device 1 stores, in the storage device 230, one or more pieces of data. One piece of data is three-dimensional position information and spectral information at each position, obtained by performing three-dimensional spectroscopic measurement of a specimen by the spectroscopy microscope 4. The CPU 201 (data obtaining unit) further stores, in the storage device 230, one or more data sets. One data set is a group of data pieces of which the three-dimensional positions have been mutually correlated. The CPU 201 specifies one or more data sets to configure a three-dimensional distribution image, based on user inputs from the input device 3.

The spectral information in the present embodiment is not restricted in particular as long as it includes wavelength information and signal intensity at each wavelength. Examples include spectroscopic spectrum signal intensity at a particular wavelength, and so forth. The three-dimensional distribution image of the spectral information may be unprocessed data obtained by performing three-dimensional spectroscopic measurement using the spectroscopy microscope 4, or may be processed data. Examples include data subjected to processing such as wavelength calibration or signal intensity standardization, and processing by multivariate analysis such as principal component analysis (PCA), independent component analysis (ICA), and discrimination analysis, and machine learning.

The three-dimensional spectroscopic measurement according to the present embodiment may involve automatically collecting the three-dimensional position information from the spectroscopy microscope 4, or the user manually recording the three-dimensional position information. In the case of the latter, one or more pieces of data can be manually created by the user using the processing device 1 to allocate the three-dimensional position information which the user has recorded to each spectral information. Additionally, the user can manually create one or more data sets by allocating the relatively correlated three-dimensional position information which the user has recorded, to each piece of data, by using the processing device 1.

There is no particular restriction to the spectroscopy microscope used to obtain spectral information. Examples of spectroscopy which the spectroscopy microscope performs include infrared spectroscopy, spontaneous Raman spectroscopy, ultraviolet/visible-light spectroscopy, and so forth. Additional examples include sum frequency generation spectroscopy, multi-photon absorption spectroscopy, and nonlinear Raman scattering spectroscopy. In a case of using a nonlinear Raman scattering microscope two lasers of different wavelength are cast on the specimen, and the nonlinear Raman scattering phenomenon, in which specific scattering occurs at the condensation point when the difference in laser frequency matches the molecular vibration frequency, is used to detect change in intensity of scattered light. Changing the wavelengths of the incident laser light and scanning the specimen yields spatial distribution information of a Raman spectrum, which is a Raman spectrum image. The nonlinear Raman scattering phenomenon is preferably used since signal intensity is markedly stronger than in a case of using the spontaneous Raman phenomenon, and is particularly effective in high-speed image acquisition. Examples of nonlinear Raman scattering spectroscopy include stimulated Raman scattering spectroscopy, coherent anti-Stokes Raman spectroscopy, and so forth, but stimulated Raman scattering spectroscopy is preferably used from the perspective of qualitativity.

Note that wavelength information may be wavelength (nm), wavenumber ($cm^{-1}$) or energy. Raman shift ($cm^{-1}$) may be used in the case of Raman spectroscopy.

Generating First Three-Dimensional Distribution Image: S420

A first three-dimensional distribution image is generated by the CPU 201 of the processing device 1, based on a specified data set. The first three-dimensional distribution image is obtained by correlating spectral information with each three-dimensional position. An arrangement may be made where only part of the spectral information (e.g., only signal intensity of a particular wavelength, only a particular main component score, etc.) is correlated. Alternatively, all information may be correlated.

Generating Second Three-Dimensional Distribution image: S430

The first three-dimensional distribution image generated by the CPU 201 of the processing device 1 is subjected to coordinate conversion, also by the CPU 201, thereby generating a second three-dimensional distribution image. In the present embodiment, the coordinate axes of the first three-dimensional distribution image are X, Y, and Z (hereinafter collectively "XYZ"). The coordinate axes of the second three-dimensional distribution image are P, Q, and R (hereinafter collectively "PQR").

This coordinate conversion will be described with reference to FIGS. 5A through 5C.

Figure 5A:
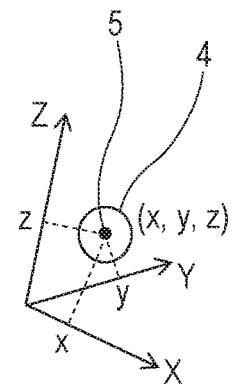
FIG. 5A is a diagram illustrating an example of converting a first three-dimensional distribution image into a two-dimensional distribution image.
Figure 5B:
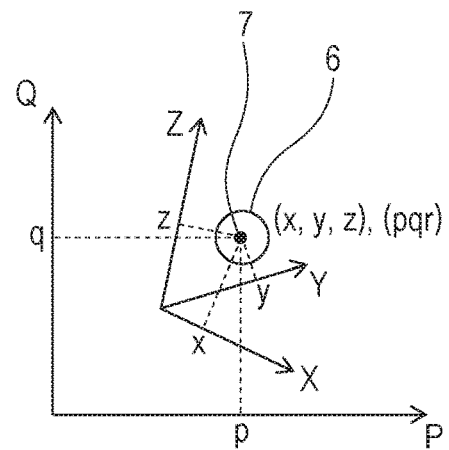
FIG. 5B is a diagram illustrating an example of converting a first three-dimensional distribution image into a two-dimensional distribution image.
Figure 5C:
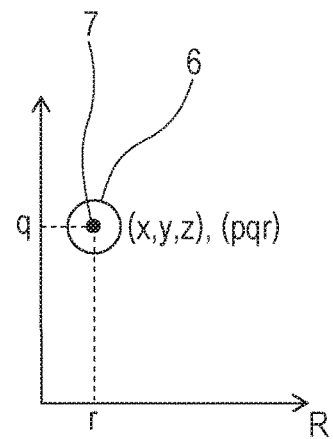
FIG. 5C is a diagram illustrating an example of converting a first three-dimensional distribution image into a two-dimensional distribution image.

A first three-dimensional distribution image 40 has coordinate axes XYZ, as illustrated in FIG. 5A. A point 5 making up the first three-dimensional distribution image 40 has position information (x, y, z) on the coordinate axes XYZ. On the other hand, FIGS. 5B and 5C illustrate a second three-dimensional distribution image 6 generated by coordinate conversion, which has coordinate axes PQR. A point 7 has position information (p, q, r) on the coordinate axes PQR. Each of the coordinate axes P and Q are equivalent to two aces perpendicular to each other in a plane including the plane of the display device 2. FIG. 5C is a schematic view observing the PQ plane from the side, where the coordinate axis R is equivalent to the depth-direction axis of the screen of the display device 2. Note that the coordinate axis R is not illustrated in FIG. 5B since it is perpendicular to the plane of the drawings, and in the same way coordinate axis P is not illustrated in FIG. 5C. The method of coordinate conversion is not restricted in particular. For example, the processing device 1 performs coordinate conversion by general vector calculation, using angles formed between coordinate axis X and coordinate axis P, coordinate axis Y and coordinate axis Q, and coordinate axis Z and coordinate axis R, and coefficient for changing scale as necessary. The coefficient in this case is to be the same value for all three coordinate axes, to maintain the relative positional relation of the points on the coordinate axes XYZ. The point 7 subjected to coordinate conversion has both three-dimensional position information (x, y, z) on the coordinate axes XYZ and three-dimensional position information (p, q, r) on the coordinate axes PQR.

All data points included in the image are subjected to coordinate conversion in the same way as point 7, and position information on the coordinate axes PQR that has been calculated is given to each piece of data. Thus, each piece of data after coordinate conversion has both three-dimensional position information on the coordinate axes XYZ and three-dimensional position information on the coordinate axes PQR.

Generating and Displaying a Two-Dimensional Projected Image: S440

The second three-dimensional distribution image is projected on a two-dimensional plane by the CPU 201 (generating unit) of the processing device 1, thereby generating a two-dimensional projected image. The two-dimensional projected image is displayed on the screen of the display device 2. Signal intensity, for example, is displayed at each data spot in the two-dimensional projected image. While the display method of signal intensity is not restricted in particular, examples include coloring each data point with different colors or tones according to signal intensity.

The two-dimensional projected image is equivalent to viewing the second three-dimensional distribution image in the R axial direction from the PQ plane. That is to say, the two-dimensional projected image is equivalent to displaying the R coordinates of each point in the second three-dimensional distribution image as 0. Now, in a case where there are multiple data points on the R axis at the same PQ coordinate position on the three-dimensional distribution image, the nearest point in the R axial direction is displayed with priority. Alternatively, transparency may be set for the colors of the data points, and displaying data points on the R axis with stronger signal intensity in an enhanced manner.

Each coordinate position in the two-dimensional projected image is provided with data of the second three-dimensional distribution image. Specifically, information of all data points existing on the R axis at each PQ coordinate position in the second three-dimensional distribution image is stored in each PQ coordinate position on the two-dimensional projected image. That is to say, each point in the QP coordinates on the two-dimensional projected image include, in addition to two-dimensional position information on the coordinate axes PQ (p, q), the three-dimensional position information on the coordinate axes PQR (p, q, r), three-dimensional position information on the coordinate axes XYZ (x, y, z), and spectral information. The number of points of data included in each point on the PQ coordinates may be zero, one, or a plurality.

Displaying of a two-dimensional projected image will be described with reference to FIGS. 6A through 7B.

Figure 6A:
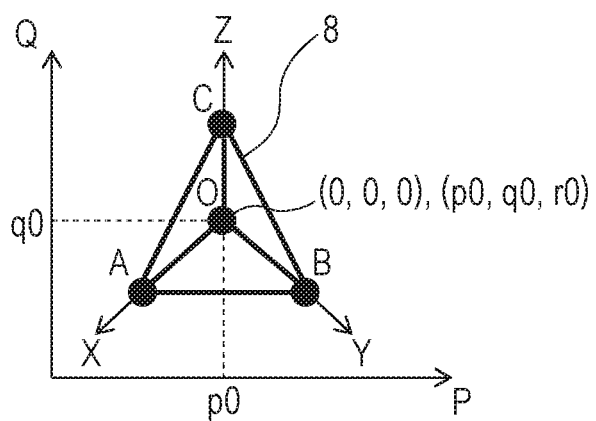
FIG. 6A is a diagram illustrating an example of a second three-dimensional distribution image.
Figure 6B:
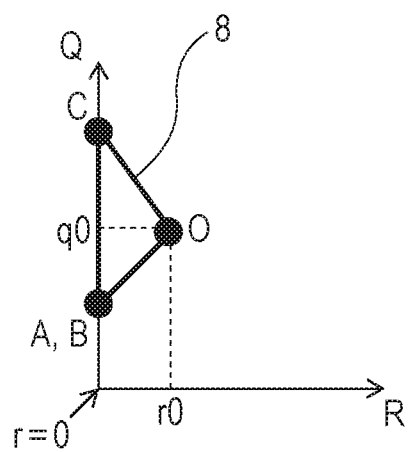
FIG. 6B is a diagram illustrating an example of a second three-dimensional distribution image.

FIGS. 6A and 6B are schematic diagrams of images after a first three-dimensional distribution image has been converted to a second three-dimensional distribution image. A second three-dimensional distribution image 8 includes data points making up line segments connecting each of points O, A, B, and C. Plane ABC is parallel to plane PQ, and line segment AB is parallel to coordinate axis P. Now, if we say that a point on the coordinate axes PQR is (p, q, r), r=0 holds for points A, B, and C, while r=r0 holds for point O as illustrated in FIG. 6B, which is to say that point O is a point which exists at a particular position in the R axis direction.

Figure 7A:
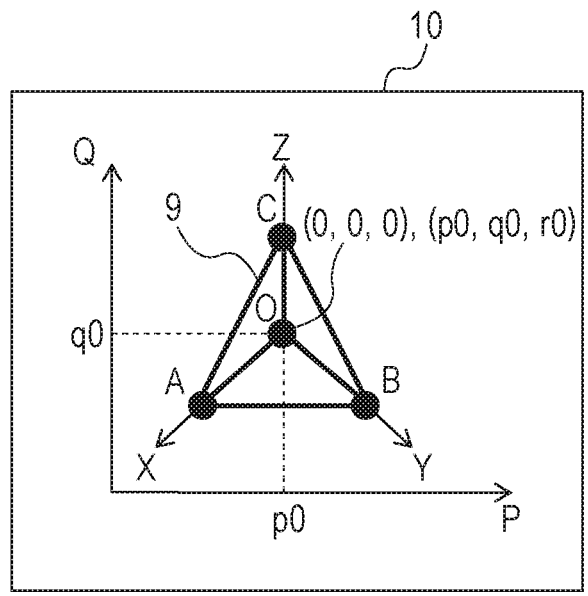
FIG. 7A is a diagram illustrating an example of a two-dimensional projection image.
Figure 7B:
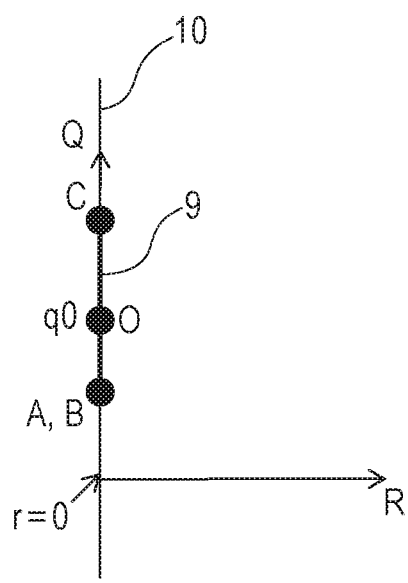
FIG. 7B is a diagram illustrating an example of a two-dimensional projection image.

FIG. 7A illustrates an example of projecting the second three-dimensional distribution image in FIGS. 6A and 6B on the PQ plane, so as to display a two-dimensional projected image 9 on a screen 10 of the display device 2. FIG. 7B is a schematic view of FIG. 7A from the side. The actual display image is only a plane, so FIG. 7B illustrates this in a virtual manner. While point O is the only point on the R axis in FIGS. 6A and 6B that is not 0, after project an image where r=0 is generated as illustrated in FIG. 7B, which is displayed on the screen of the display device 2. However, the data of the PQR coordinates stored in point O itself is not rewritten, as illustrated in FIG. 7A.

Note that the directions of the coordinate axes XYZ for display, or the range of the scale, of the displayed two-dimensional projected image may be optionally adjusted using the input device 3. The three-dimensional position information on the coordinate axes PQR (p, q, r) may be recalculated based on the adjusted image, and updated. Adjustment of the directions of the coordinate axes XYZ for display, and range of the scale of the image, may be performed by an assigned function to the input device 3. For example, in a case where the input device 3 is a mouse, a function may be assigned to the mouse where left-clicking and dragging the mouse rotates or translates the image, and rotating the wheel member enlarges or reduces the image. Another example of the input device 3 is a trackball having functions of image direction rotation, translation, enlargement, and reduction.

The number of two-dimensional projected images generated and display may be one or may be a plurality. In the case of a plurality, in addition to the two-dimensional projected image projected on the PQ plane, there may be a two-dimensional projected image projected on the RQ plane which is the side of the PQ plane, and a two-dimensional projected image projected on the PR plane which is the base of the PQ plane, for example. Further, there may be two-dimensional projected images projected on planes viewed from the opposite direction in the perpendicular direction to each of the PQ plane, RQ plane, and PR plane ((−P)Q plane, (−R)Q plane, and P(−R) plane). In a case where the PQ plane is taken as a frontal view in third angle projection, the remaining five planes are the right side view, top view, rear view, left side view, and bottom view. Another example of multiple two-dimensional projected images is multiple images adjusted regarding the direction of coordinate axes XYZ of display or size ranges, and displayed on the PQ plane. Obtaining such multiple two-dimensional projected images enables the three-dimensional data to be visualized from multiple planes, and accordingly, later-described selection of a plane region (S450) and selection of a second feature region (S470) can be performed more appropriately.

Selecting Plane Region within Two-Dimensional Projected Image: S450

A plane region (two-dimensional region) within the PQ coordinate plane is selected by the user operating the processing device 1 with regard to a two-dimensional projected image displayed on the screen of the display device 2, with the intent to select a range for searching for feature regions in the three-dimensional distribution image. In a case where there are multiple two-dimensional projected images displayed, the user uses the input device 3 to select any image from the multiple images from which to select a plane region. In this case, the selected image may be highlighted to indicate that the image is a state where a plane region can be selected. This highlighting may be performed using symbols, frames or the like as example, but is not restricted in particular. In the present embodiment, position information of the plane region input to perform searching for feature regions will be referred to as "region selection information".

The selection of an image for selecting a plane region, and input of region selecting information, is preferably performed by displaying a pointer on the display screen of the display device 2 and operating the pointer using the input device 3 such as a mouse or the like, from the perspective of operability. The pointer can be used to perform operations of identifying and selecting each individual data point on the display screen. The pointer may be a symbol in the form of an arrow, or any other image. Note that alternatively, selection of a plane region may be performed by numerical value input from a keyboard, or the like.

The plane region is a region including at least one point on the PQ coordinates. There is no particular restriction regarding the size or shape of the region; this may be selected a suitable with the usage. The region may be in the form of a straight line, a circle, a triangle, a square, a polygon, or any other shape. There is no particular restriction regarding the selection method of the region, such as operating a pointer with a mouse, selecting one data point by numeral input or the like and further selecting a region centered on that point. Further, a shape may be selected, and the region selected by operating the pointer with a mouse or inputting numeral values such as radius, length of sides, or the like. Further, an arrangement may be made where the pointer is operated by a mouse, and the region is specified by polyline or freehand.

Recognizing Feature Regions and Positional Information Thereof: S460

Upon the user selecting a plane region within the PQ plane of the two-dimensional projected image, the CPU 201 (information obtaining unit) obtains the position information of that plane region. The CPU 201 then selects a space (three-dimensional region) including all data points existing in the depth direction from that plane region (in the plus/ minus directions on the coordinate axis R), as the search target range in the feature region. That is to say, while the user views the image as a two-dimensional projected image on the screen, the search of the feature region is performed on the second three-dimensional distribution image. Feature regions are recognized by the CPU 201 in this space, and three-dimensional position information of the feature regions is recognized. A feature region in the present specification is a region which satisfies predetermined feature conditions with regard to at least one of spectral information and three-dimensional form information.

In a case of multiple feature regions existing within the search target range, the multiple feature regions are recognized. A feature region may be one data point, or may be one region including multiple data points. Also, a feature region may be two or more data points that are not adjacent, or may be multiple regions made up of the multiple data points. The feature conditions may be set by the processing device 1 beforehand, or the user may set the feature conditions anew using the input device 3.

Two feature conditions (first and second feature conditions are used in the present specification.

The first feature condition is a condition relating to signal intensity in the spectral information. Signal intensity may be regarding one signal of one particular wavelength, or may be signals of particular multiple wavelengths. Further, signal intensity may be cumulative signals at a particular wavelength range. A spectroscopic spectrum reflects molecular structure information such as the molecule's functional group, main backbone, conjugation length, and so forth. Accordingly, signal intensity at a particular wavelength (band) reflects information of the amount of a particular molecule. Thus, using signal intensity at a particular wavelength (band) as a feature condition is effective in cases of focusing on the amount of particular molecules.

In a case of using the first feature condition, the CPU 201 searches regions where the signal intensity exceeds the threshold value within the selected space. At the time of searching, the CPU 201 first creates a list of data combining the signal intensities and corresponding three-dimensional position information. Next, the CPU 201 sorts the list by signal intensity, and thus extracts combinations of signal intensity exceeding the threshold value, as search results. The threshold may be the values of signal intensity, or may be the relative order of signal intensity. Thus, feature regions and three-dimensional position information thereof are recognized.

The second feature condition is a condition relating to three-dimensional form. This three-dimensional form includes at least one of form and size. The second feature condition focuses on form features of structures included in the specimen. For example, in tissue, cell nuclei are spherical, vascular channels are tubular, and fiber are linear. Even if the form is the same the size differs depending on the structure, such as cell nuclei and blood cells having different sizes though both are spherical. This also differs from one organ to another, from one organism type to another, and further differs depending on physiological state and pathological condition.

In a case of using the second feature condition, the CPU 201 searches for particular three-dimensional form information within the selected space. At the time of searching, the CPU 201 first sets reference three-dimensional form information. Next, the CPU 201 searches within the selected space for a region similar to the reference three-dimensional form information. The similarity of three-dimensional form information at each region as to the reference three-dimensional form information is evaluated, and a list is created of data combining the similarity and the three-dimensional position information of the region corresponding to the similarity. While the calculation method of similarity is not restricted in particular, one example is to use similarity obtained by dividing the difference in volume of the three-dimensional form in each data region by the volume of a three-dimensional form that has been set. The list is then sorted by similarity, and combinations of data satisfying a particular threshold regarding similarity are extracted as search results. The threshold may be a similarity value, or may be a relative order of the similarities. Thus, feature regions and three-dimensional position information thereof are recognized.

The forms used for the second feature condition may be common form such as spheres, cubes, cuboids, cones, cylinders, or the like, or may be any form. Any size may be specified. If there is a database storing information relating to candidate forms and sizes of structures, the database may be used as the feature conditions. The form of a particular region in the three-dimensional distribution image may be used as a feature condition.

When using the second feature condition, the signal intensity according to the first feature condition may be used in combination as a threshold here as well, or the regions may be divided into two levels, of whether exceeding the threshold of the first feature condition or not, and only using the three-dimensional form information of those exceeding the threshold.

Further, signals indicating ranking based on signal intensity or three-dimensional form is given to the feature regions recognized in this step. The symbols indicating ranking may be given in order from the highest signal intensity, or in order from the highest similarity to any specified three-dimensional form or three-dimensional database. There is no restriction to the symbols representing the ranking; examples include numerals and alphabetical characters.

There is no particular restriction in the number of feature regions recognized using the first or second feature conditions described above. The CPU 201 temporarily stores the recognized feature regions in the storage device 230.

Selection and Display of Feature Region: 470

The CPU 201 selects, from the feature regions recognized in S460 (first feature region) at least one feature region (second feature region), and displays the at least one feature region that has been selected (second feature region) on the two-dimensional plane of the display device 2. The displayed second feature region is the feature region which the user has specified (as a result). To facilitate description, a feature region recognized in S460 is referred to as "first feature region", and a feature region selected and displayed in S470 is referred to as "second feature region".

All first feature regions recognized in S460 may be displayed as second feature regions, or only part of the first feature regions recognized in S460 may be displayed as second feature regions. Selection of the second feature region may be performed based on the ranking given in S460.

In a case where only part of the first feature regions is displayed, any region in the first feature regions not displayed may be selected so as to replace a first feature region being displayed, so as to newly be taken as a second feature region and displayed. This selection is performed using the input device 3. In a case where the input device 3 is a mouse, for example, the CPU 201 obtains user instructions according to clicking of the mouse buttons or spinning of the wheel member, sequentially selecting a non-displayed first feature region based on the instructions, and displaying the selected feature regions as second feature regions in order.

The CPU 201 displays the second feature region in an highlighted manner in the two-dimensional projected image on the display device 2, so that the user can readily visually distinguish between the second feature region and regions other than the second feature region. The method of highlighting is not restricted in particular. For example, methods may be used such as raising the brightness of the second feature region, changing the color of the second feature region, placing a symbol such as an arrow nearby the second feature region, or the like. Alternatively, an image of the area around the second feature region including the second feature region may be opened as a second window. Further, methods may be used such as not displaying regions other than the second feature region, lowering the brightness of regions other than the second feature region, changing the color of regions other than the second feature region, and so forth.

Another example of a preferable highlighting method is as follows. Upon the user moving the pointer onto the two-dimensional projected image to select a plane region, the CPU 201 displays the state of the pointer moving to the second feature region. The state of moving may be indicated by a dotted line segment connecting the selected portion and the position in the second feature region, or pointers may be displayed on both the selected position and the position of the second feature region, or the movement of the pointer may be displayed as a moving image or the like. The pointer is moved by the CPU 201 of the processing device 1. Displaying the state of movement of the pointer facilitates comparison between the plane region selection which the user performs, and recognition, selection, and display of results of the feature region which the CPU 201 performs. Consequently, the user can recognize more easily whether the feature region which the user intended has been recognized as a second feature region or not.

The number of second feature regions selected and displayed in this step may be one or multiple. In a case of multiple second feature regions, the CPU 201 preferably displays symbols indicating the ranking given to the first feature regions near the second feature regions. Also, in a case of multiple second feature regions, the processing device 1 preferably has a function to further select part of the feature regions out of the multiple second feature regions to be displayed highlighted even further. More preferably, the processing device 1 preferably has a function to display, out of the multiple second feature region, feature regions regarding which highlighting is desired, so as to be selected, in order and enhanced following the depth direction of the screen of the display device 2. The selection thereof is performed using the input device 3 to which predetermined functions have been assigned. For example, in a case where the input device 3 is a mouse, the user can made this selection by clocking the mouse button or spinning the wheel member. Examples of preferably assigned predetermined functions include rotation of the mouse wheel member sequentially selecting multiple second feature regions distributed in the depth direction of the screen, and left-clicking deciding the second feature region to be a feature region of interest and highlighted. In this state where the second feature regions are overlaid in the depth direction of the screen in particular, the user can identify each second feature region and appropriately select a second feature region of interest due to this function. Examples of display methods to further highlight a part of the feature regions out of the second feature regions include changing the brightness or color of the symbols indicating ranking, and so forth.

The processing device 1 preferably has a function such that when displaying the second feature region, the display screen can be changed so that the user can view the second feature region from a different angle. This changing of the display screen facilitates distinguishing structures in cases where distinguishing structures is difficult in the initially displayed display screen, and in cases where multiple feature regions are displayed overlaid in the R axis direction. Specifically, the processing device 1 preferably has a function to rotate the image of the displayed second feature region or to display side views, top and bottom views, and rear view of the initially display image by third angle projection, by operating the input device 3 such as a mouse or keyboard. Rotating and switching of displayed images may also be performed by operating an input device 3 such as a mouse or trackball or the like to which predetermined functions have been assigned.

In a case where there are multiple two-dimensional projected images displayed in S440, the processing device 1 preferably has a function where the second feature region is displayed in all images. The processing device 1 further preferably has a function where the user can optionally select an image to operate so as to select and display a second feature region. Additionally, the processing device 1 preferably has a function to reselect an image to operate so as to select and display a second feature region in the process of selecting the second feature region, by operating the input device 3. These functions allow the user to select a second feature region by selecting images more readily distinguished by the user, so selection precision and throughput improve. The processing device 1 preferably has a function to further compare the displayed second feature region with other data. There is no restriction in particular regarding the data to be compared; this may be data included in the second three-dimensional distribution image, or data included in a database.

A region recognized as being data similar to the second feature region (similar feature region), as the result of comparing data included in the second feature region with data not included in the second feature region but included in the second three-dimensional distribution image, may be displayed in addition to the second feature region. Displaying similar feature regions may improve precision of distinguishing feature regions and analysis in some cases.

An example of processing the three-dimensional distribution of spectral information obtained by a stimulated Raman scattering spectroscopy microscope, and displaying a cell nucleus included in the tissue as a feature region will be described with reference to FIGS. 8A through 8E, in light of the flowchart in FIG. 4 described above.

A cell nucleus exhibits a strong signal around Raman shift of 2930 cm$^{-1}$, so the processing device 1 first generates a three-dimensional distribution image of signal intensities at that Raman shift value (first three-dimensional distribution image). Specifically, the processing device 1 generates first three-dimensional distribution image based on a dataset and Raman shift value specified by the user.

Next, the processing device 1 performs coordinate conversion of the first three-dimensional distribution image, thereby generating a second three-dimensional distribution image.

Figure 8A:
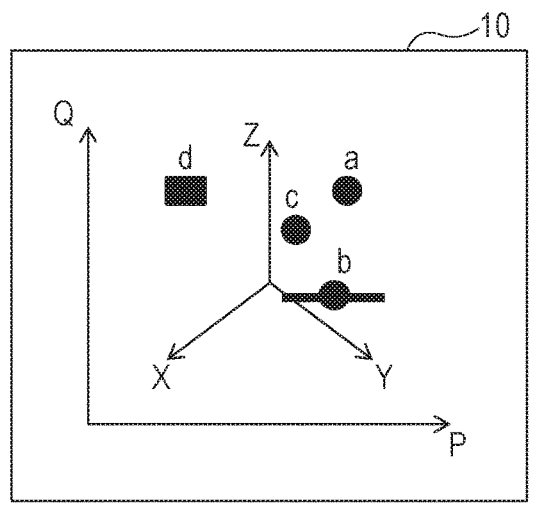
FIG. 8A is a diagram illustrating an example of displaying a feature region on a two-dimensional projection image.

The processing device 1 then projects the second three-dimensional distribution image on a two-dimensional plane screen, thereby generating a two-dimensional projected image such as illustrated in FIG. 8A. Note that FIG. 8A is an example of a two-dimensional projected image displayed on the screen of the display device 2.

The Raman shift value exhibits a certain level of signal intensity at the cytoplast and other structures as well. The user specifies a region for regions a, b, c, and d, displayed in the two-dimensional projected image illustrated in FIG. 8A, and confirms the three-dimensional form and Raman spectrum thereof, so as to distinguish the cell nucleus from the region. However, the three-dimensional form is not visually confirmable from the two-dimensional projected image, and moreover two regions b-1 and b-2 of region b are displayed overlapped so region specification is troublesome.

Figure 8B:
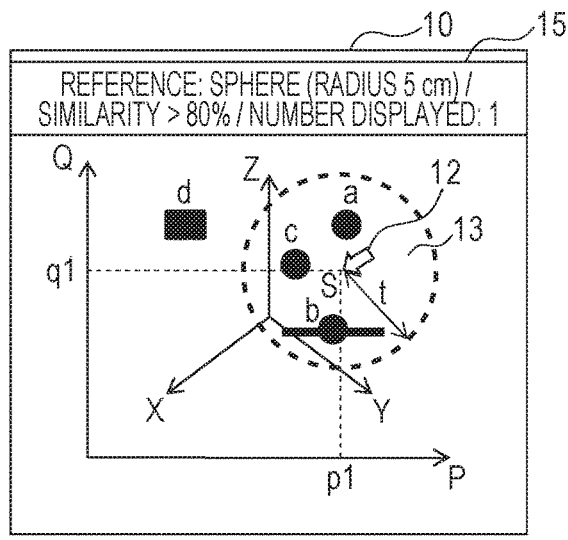
FIG. 8B is a FIG. 8B is a diagram illustrating an example of displaying a feature region on a two-dimensional projection image.

Accordingly, the user selects a plane region 13 including the candidate regions using a pointer 12, as illustrated in FIG. 8B. The plane region 13 is a circular region having a radius of t, centered on a point S (p1, q1) on the PQ coordinates plane. Accordingly, the selected plane region 13, and space 14 including all data points existing in the depth-wise direction (coordinate axis R) of the screen in the three-dimensional distribution image illustrated in FIG. 8C, can be selected as search target regions to search for feature regions. Besides selecting the plane region, the user specifies a sphere as the reference three-dimensional form, specifies a threshold value for similarity with a sphere, and specifies the number of feature regions to be displayed. A display region 15 in the screen 10 displays the three-dimensional form, similarity, and number of displays, which the user has specified.

Figure 8C:
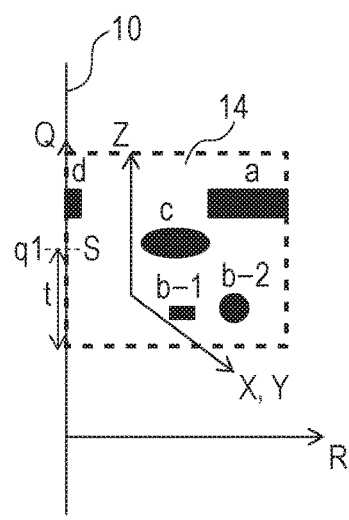
FIG. 8C is a diagram illustrating an example of displaying a feature region on a two-dimensional projection image.

Next, the processing device 1 searches within the space 14, using a specified reference form and similarity as feature conditions. As illustrated in FIG. 8C, the second three-dimensional distribution image stores the region b as three-dimensional position information divided into the two regions b-1 and b-2 of which the depth-wise positions are not the same. Accordingly, the search of the space 14 includes the three-dimensional position information of the region b divided into the two regions b-1 and b-2, and these are separate search targets. As a result of the search, the region b-2 which is close to a sphere is recognized as a first feature region, and moreover the three-dimensional position information thereof is recognized. More specifically, data which is a combination of the Raman spectrum information of the region b-2 and the three-dimensional position information of the region b-2, is recorded in the processing device 1 (storage device 230). While regions a and c are circular in the two-dimensional projected image, the three-dimensional forms are not spherical, and accordingly are not recognized as first feature regions in the present embodiment.

Figure 8D:
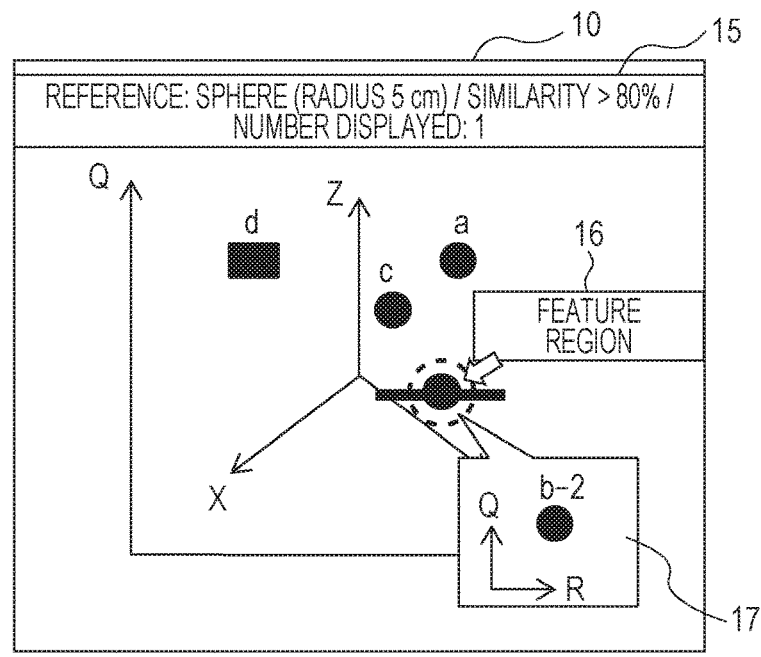
FIG. 8D is a diagram illustrating an example of displaying a feature region on a two-dimensional projection image.

Next, the first feature region b-2 is displayed highlighted on the screen as a second feature region as illustrated in FIG. 8D, based on the number of display regions set by the user. In the present embodiment, the processing device 1 automatically moves the pointer 12 onto the second feature region b-2, and also displays an image 16 nearby, and further displays a separate window 17, thereby highlighting that the region b-2 is a second feature region. As illustrated in FIG. 8D, the window 17 displays the QR plane. This window 17 is preferably displayed when different regions overlap in the PQ plane. Note that this second feature region is the feature region which the user has specified.

Thus, overlapping in the region b can be displayed in a separated manner, and also the regions a and c are not erroneously recognized as feature regions, so the user can easily specify the feature region b-2.

Figure 8E:
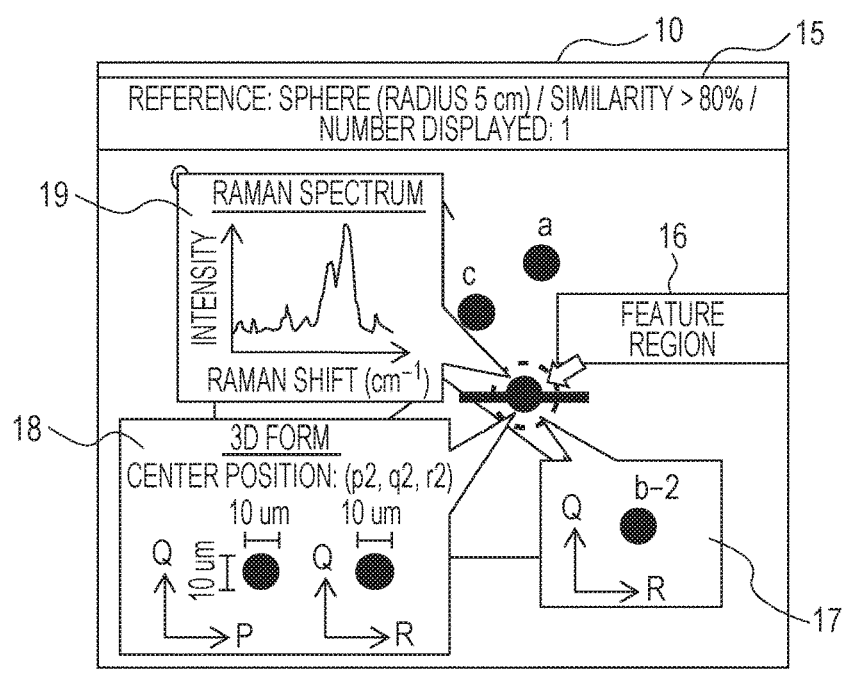
FIG. 8E is a diagram illustrating an example of displaying a feature region on a two-dimensional projection image.

The user can continue to confirm the three-dimensional form and Raman spectrum of the feature region b-2 as illustrated in FIG. 8E, and thus distinguish the cell nucleus. Note that the processing device 1 obtains user input information from the input device 3 and displays a window 18 displaying the three-dimensional form of the second feature region, and a window 19 displaying the Raman spectrum in the second feature region, upon the screen 10.

Thus, according to the microscope system of the present embodiment, depth-wise information is added to the two-dimensional projected image, so three-dimensional forms and overlapping feature regions can be identified. Accordingly, appropriate specification of feature regions can be easily performed, and analysis precision is improved.

Note that spectral information included in the second feature region is preferably displayed along with the display of the second feature region. Display of spectral information may be performed regarding all second feature regions being displayed, or only regarding a specific feature region.

Display of spectral information may be performed at the same time as display of the feature region, or may be based on input after the feature region is displayed. For example, an arrangement may be made where, in a case where there are multiple feature regions displayed, the three-dimensional position information and spectral information are not displayed at that time, and when the user selects one feature region of the multiple feature regions, the three-dimensional position information and spectral information of that feature region are displayed.

The displayed spectral information may be a spectroscopic spectrum, or data made up of a particular wavelength range and signal intensity, or maximal wavelength and minimal wavelength. One or more of these may be used, and may be selected as appropriate in accordance with the usage as described next.

In a case of performing molecular identification in a feature region, by matching with a database or the like, the spectroscopic spectrum is preferably displayed. Molecular identification by spectral information may be difficult if the only information is signal intensity of a particular wavelength. Accordingly, the entire spectrum is preferably displayed.

In a case of obtaining quantitative information such as molecule concentration in the feature region, the particular wavelength range and the signal intensity at the particular wavelength range is preferably displayed. If the target molecule, and the wavelength information thereof are known, quantitative determination may be easily made using signal intensity. Accordingly, data made up of the particular wavelength range and signal intensity is preferably displayed.

In a case of confirming features of molecules in the feature region, the maximal wavelength (or minimal wavelength) in the spectroscopic spectrum is preferably displayed. If a general idea of molecules in the feature region has been obtained, the maximal wavelength (or minimal wavelength) may be an easy criterion for confirmation thereof. Accordingly, the maximal wavelength (or minimal wavelength) in the spectroscopic spectrum is preferably displayed.

Displaying such spectral information included in the feature region enables spectral information to be visually configured in addition to the form information of the feature region, whereby analysis throughput can be improved.

Further, when displaying the second feature region, three-dimensional position information of the feature region is preferably display together.

Display of the three-dimensional position information may be a point or range on the XYZ coordinates, based on the original data, or may be a point or range on the PQR coordinates configured by coordinate conversion, or may be both. Alternatively, an arrangement may be made where only perpendiculars from each point or the range to the XYZ coordinates or PQ coordinates displayed on the two-dimensional plane on the display device 2, and intersection points of the perpendiculars and the coordinates, are displayed.

Thus, a display enabling visual confirmation of three-dimensional position information is performed, so even in cases where multiple feature regions are overlaid in the depth direction, the user can clearly understand the difference. Accordingly, human error in distinguishing structures can be reduced.

Additionally, candidate names of structures included in a second feature region being displayed are also preferably displayed. Structures include any of structures classified as organs, cell assemblies, cells, cell nuclei, cytoplast, cell membranes, adipose tissue, basal membranes, organelles, inclusion bodies; sections existing within the structures; and molecules, functional groups, and atoms included in the structures or sections. The displayed candidate names may be just one, or a combination of multiple names associated with the one name (relation of higher/lower order concept or spatial inclusion).

The displayed candidate names may be information stored in a database used in S460, or may be the results of comparing the obtained second feature region with the database again. In a case of comparing with the database again, the information used to this end may be spectral information, three-dimensional function information, or both. The database with which comparison is made may be a database with no information updating, or a database with a learning function to update information.

In a case of taking one candidate name or a combination of multiple names associated with one name as one candidate, display may be made of one candidate or multiple candidates. In the case of multiple candidates being displayed, the candidates are preferably displayed in order of similarity with the database.

The candidate name displayed may be the name of an organism type associated with the structure.

In a case of displaying a similar region with the feature region, any of spectral information, three-dimensional position information, and candidate name of structure included in similar region, may be displayed together, in the same way as with the second feature region.

Other Embodiments

Embodiments of the present invention also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing device configured to process spectral information, comprising:
    a data obtaining unit configured to obtain three-dimensional distribution data of spectral information;
    a generating unit configured to generate two-dimensional image data from the three-dimensional distribution data of spectral information;
    a display unit;
    a display control unit configured to display the two-dimensional image on the display unit;
    an information obtaining unit configured to obtain position information of a two-dimensional region which a user has selected from the two-dimensional image; and
    an extracting unit configured to extract, from a three-dimensional region corresponding to the two-dimensional region, in the three-dimensional distribution of spectral information, a feature region satisfying a predetermined feature condition.

2. The information processing device according to claim 1,
    wherein the display control unit displays the feature region on the display unit, so that the user can distinguish between the feature region and a region other than the feature region.

3. The information processing device according to claim 2,
    wherein the display control unit displays an image of the feature region on the display unit in a highlighted manner.

4. The information processing device according to claim 3,
    wherein the information obtaining unit obtains position information of the two-dimensional region which the user has selected using a pointer displayed on the display unit; and
    wherein the display control unit displays the pointer nearby the image of the feature region, thereby displaying the image of the feature region in a highlighted manner.

5. The information processing device according to claim 1,
    wherein the display control unit displays the spectral information of the feature region on the display unit.

6. The information processing device according to claim 5,
    wherein the spectral information is information obtained by Raman spectroscopy.

7. The information processing device according to claim 5,
    wherein the two-dimensional image is an image obtained by projecting a three-dimensional distribution image of the spectral information onto a plane.

8. The information processing device according to claim 1,
wherein the display control unit displays position information of the feature region in the depth-wise direction, on the display unit.

9. The information processing device according to claim 1,
wherein the extracting unit extracts a plurality of feature regions from the three-dimensional region.

10. The information processing device according to claim 9,
wherein the information obtaining unit obtains information relating to which feature region of the plurality of feature regions the user wants to display;
and wherein the display control unit displays an image of the feature region which the user wants to display, on the display unit.

11. The information processing device according to claim 9,
wherein the information obtaining unit obtains user instructions, to display on the display unit a feature region not displayed on the display unit, instead of a feature region displayed on the display unit, out of the plurality of feature regions; and
wherein the display control unit displays, on the display unit, an image of the feature region not displayed on the display unit, instead of an image of a feature region displayed on the display unit, based on the instructions.

12. The information processing device according to claim 1,
wherein the predetermined feature condition is a condition relating to signal intensity.

13. The information processing device according to claim 1,
wherein the predetermined feature condition is a condition relating to three-dimensional form.

14. The information processing device according to claim 1,
wherein the spectral information displayed on the display unit includes a spectroscopic spectrum.

15. The information processing device according to claim 1,
wherein the spectral information displayed on the display unit includes signal intensity of light of a particular wavelength range.

16. The information processing device according to claim 1,
wherein the spectral information displayed on the display unit includes a maximal wavelength or a minimal wavelength.

17. The information processing device according to claim 1,
wherein the spectral information displayed on the display unit includes a principal component score.

18. The information processing device according to claim 1,
wherein the display control unit displays a candidate name of a structure included in the feature region on the display unit.

19. A microscope system comprising:
a microscope configured to obtain spectral information; and
the information processing device according to claim 1, configured to process the spectral information.

20. An information processing method to process spectral information, comprising:
obtaining three-dimensional distribution data of spectral information;
generating, using a processor, two-dimensional image data from the three-dimensional distribution data of spectral information, the two-dimensional image data being used for displaying a two-dimensional image on a display unit;
displaying the two-dimensional image on the display unit;
obtaining position information of a two-dimensional region which a user has selected from the two-dimensional image;
extracting, from a three-dimensional region corresponding to the two-dimensional region, in the three-dimensional distribution of spectral information, a feature region satisfying a predetermined feature condition; and
displaying the feature region on the display unit.

21. A non-transitory computer-readable recording medium, in which is recorded a program to cause a computer to perform an information processing method to process spectral information, the method comprising:
obtaining three-dimensional distribution data of spectral information;
generating two-dimensional image data from the three-dimensional distribution data of spectral information, the two-dimensional image data being used for displaying a two-dimensional image on a display unit;
displaying the two-dimensional image on the display unit;
obtaining position information of a two-dimensional region which a user has selected from the two-dimensional image;
extracting, from a three-dimensional region corresponding to the two-dimensional region, in the three-dimensional distribution of spectral information, a feature region satisfying a predetermined feature condition; and
displaying the feature region on the display unit.

* * * * *